United States Patent
Fang et al.

(10) Patent No.: US 11,401,331 B2
(45) Date of Patent: Aug. 2, 2022

(54) ANTI-PD-L1 ANTIBODY AND IL-7 FUSIONS

(71) Applicant: I-Mab Biopharma US Limited, Gaithersburg, MD (US)

(72) Inventors: Lei Fang, Shanghai (CN); Feifei Cui, Shanghai (CN); Haijuan Gu, Shanghai (CN); Zhengyi Wang, Shanghai (CN); Bingshi Guo, Shanghai (CN); Jingwu Zang, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 219 days.

(21) Appl. No.: 16/482,023

(22) PCT Filed: Jan. 25, 2019

(86) PCT No.: PCT/CN2019/073264
§ 371 (c)(1),
(2) Date: Jul. 30, 2019

(87) PCT Pub. No.: WO2019/144945
PCT Pub. Date: Aug. 1, 2019

(65) Prior Publication Data
US 2019/0352405 A1    Nov. 21, 2019

(30) Foreign Application Priority Data
Jan. 25, 2018  (WO) ................ PCT/CN2018/074121

(51) Int. Cl.
*C07K 14/46* (2006.01)
*C07K 16/28* (2006.01)
*C07K 14/54* (2006.01)
*A61P 35/00* (2006.01)

(52) U.S. Cl.
CPC .......... *C07K 16/2827* (2013.01); *A61P 35/00* (2018.01); *C07K 14/5418* (2013.01); *C07K 16/2818* (2013.01); *C07K 2317/31* (2013.01); *C07K 2317/55* (2013.01); *C07K 2317/565* (2013.01); *C07K 2317/622* (2013.01); *C07K 2319/32* (2013.01)

(58) Field of Classification Search
CPC combination set(s) only.
See application file for complete search history.

(56) References Cited

U.S. PATENT DOCUMENTS

| | | | |
|---|---|---|---|
| 9,567,399 B1 * | 2/2017 | Campbell | C07K 16/2827 |
| 10,059,769 B2 * | 8/2018 | Fang | A61K 35/17 |
| 10,208,119 B2 * | 2/2019 | Fang | A61P 35/00 |
| 10,723,799 B2 * | 7/2020 | Fang | A61P 31/20 |

FOREIGN PATENT DOCUMENTS

| | | |
|---|---|---|
| CN | 101072793 | 11/2007 |
| CN | 101228275 | 7/2008 |
| CN | 102575227 A | 7/2012 |
| CN | 104768969 A | 7/2015 |
| CN | 105837690 A | 8/2016 |
| CN | 106659742 A | 5/2017 |
| CN | 107488229 | 12/2017 |
| CN | 107519499 A | 12/2017 |
| WO | WO 02/072631 | 9/2002 |
| WO | 2017215590 | 12/2017 |
| WO | 2017220990 | 12/2017 |
| WO | WO 2017/215590 | * 12/2017 |

OTHER PUBLICATIONS

International Search Report and Written Opinion of PCT/CN2019/073264 dated Apr. 24, 2019 and Apr. 19, 2019 (19 pages).
Uniprot, "UniProtKB-P13232 (IL7_HUMAN)", https://www.uniprot.org/uniprot/P13232, Jan. 1, 1990, 7 pages.
Extended European Search Report for EP Application No. 19730102.1 dated Jun. 15, 2020, 12 pages.
Chen et al., "Therapeutic efficacy of an anti-PD-L1 antibody based immunocytokine in a metastatic mouse model of colorectal cancer", Biochemical and Biophysical Research Communication, vol. 480, No. 2, 2016, pp. 160-165.
Lin, "The Role of IL-7 in immunity and cancer", Anticancer Research, vol. 37. No. 3, 2017, pp. 963-968.
Pasche et al., "Cloning and characterization of novel tumor-targeting immunocytokines based on murine IL7", Journal of Biotechnology, vol. 154, No. 1, 2011, pp. 84-92.
Cosenza et al., "Comparitive model building in interleukin-7 using interleukin-4 as a template: A structural hypothesis that displays atypical surface chemistry in helix D important for receptor activation", Protein Science, vol. 9, No. 5, 2000, pp. 916-926.
McElroy et al., "Structural and Biophysical Studies of the Human IL-7/IL-7R@a Complex", Structure, vol. 17, No. 1, 2009, pp. 54-65.
Vanderspek et al., "Structure Function Analysis of Interleukin 7: Requirement for an Aromatic Ring at Position 143 of Helix D", Cytokine, vol. 17, No. 5, 2002, pp. 227-233.

* cited by examiner

*Primary Examiner* — Laura B Goddard
(74) *Attorney, Agent, or Firm* — Sheppard Mullin Richter & Hampton LLP

(57) ABSTRACT

Provided are fusion molecule having a PD-L1 inhibitor fused to a human IL-7 protein or fragment thereof through a peptide linker. The disclosed fusion molecules exhibited synergistic anti-tumor effects.

6 Claims, 13 Drawing Sheets
Specification includes a Sequence Listing.

ANTI-PD-L1 ANTIBODY AND IL-7 FUSIONS

CROSS REFERENCE TO RELATED APPLICATIONS

The present application is the U.S. national stage application of International Application PCT/CN2019/073264, filed Jan. 25, 2019, which claims priority to International Application PCT/CN2018/074121, filed Jan. 25, 2018, the contents of each of which are incorporated herein by reference in their entireties in the present disclosure.

BACKGROUND

Interleukin 7 (IL-7) is a hematopoietic growth factor secreted by stromal cells in the bone marrow and thymus. IL-7 stimulates the differentiation of multipotent hematopoietic stem cells into lymphoid progenitor cells. It also stimulates proliferation of all cells in the lymphoid lineage (B cells, T cells and NK cells). IL-7 is a cytokine important for B and T cell development. This cytokine and the hepatocyte growth factor (HGF) form a heterodimer that functions as a pre-pro-B cell growth-stimulating factor. This cytokine is found to be a cofactor for V(D)J rearrangement of the T cell receptor beta (TCRß) during early T cell development. This cytokine can be produced locally by intestinal epithelial and epithelial goblet cells, and may serve as a regulatory factor for intestinal mucosal lymphocytes.

Recombinant IL-7 has been safely administered to patients in several phase I and II clinical trials. A human study of IL-7 in patients with cancer demonstrated that administration of this cytokine can transiently disrupt the homeostasis of both CD8$^+$ and CD4$^+$ T cells with a commensurate decrease in the percentage of CD4$^+$ CD25$^+$ Foxp3$^+$ T regulatory cells. No objective cancer regression, however, was observed.

Programmed death-ligand 1 (PD-L1), also known as cluster of differentiation 274 (CD274) or B7 homolog 1 (B7-H1), is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

It has been shown that upregulation of PD-L1 may allow cancers to evade the host immune system. An analysis of tumor specimens from patients with renal cell carcinoma found that high tumor expression of PD-L1 was associated with increased tumor aggressiveness and an increased risk of death. Many PD-L1 inhibitors are in development as immuno-oncology therapies and are showing good results in clinical trials.

In addition to treatment of cancers, PD-L1 inhibition has also shown promises in treating infectious diseases. In a mouse model of intracellular infection, *L. monocytogenes* induced PD-L1 protein expression in T cells, NK cells, and macrophages. PD-L1 blockade (e.g., using blocking antibodies) resulted in increased mortality for infected mice. Blockade reduced TNFα and nitric oxide production by macrophages, reduced granzyme B production by NK cells, and decreased proliferation of *L. monocytogenes* antigen-specific CD8 T cells (but not CD4 T cells). This evidence suggests that PD-L1 acts as a positive costimulatory molecule in intracellular infection.

SUMMARY

The present disclosure demonstrates that when a PD-L1 inhibitor is fused to an IL-7 protein through a peptide linker, the fusion molecule can maintain the binding activities of both components. Further, the fusion molecule exhibited comparable activities to the combination of both proteins alone. Moreover, improved results could be achieved with mutant IL-7 proteins having reduced activities.

In accordance with one embodiment of the present disclosure, therefore, provided is a fusion molecule comprising a PD-L1 inhibitor fused to a human IL-7 protein or fragment thereof through a peptide linker. In some embodiments, the peptide linker has from 5 to 100 amino acid residues. In some embodiments, the peptide linker has from 10-75 amino acids. In some embodiments, at least 20% of the amino acid residues of peptide linker are amino acid residues selected from the group consisting of alanine, glycine, cysteine, and serine. In some embodiments, at least 40% of the amino acid residues of peptide linker are amino acid residues selected from the group consisting of alanine, glycine, cysteine, and serine. In some embodiments, the peptide linker comprises an amino acid sequence selected from the group consisting SEQ ID NO: 1-5.

In some embodiments, the PD-L1 inhibitor is a decoy PD-1 protein, such as an inactive PD-1 that binds PD-L1. In some embodiments, the PD-L1 inhibitor is an anti-PD-L1 antibody of fragment thereof. In some embodiments, the anti-PD-L1 antibody is of an isotype of IgG, IgM, IgA, IgE or IgD. In some embodiments, the fragment of the anti-PD-L1 antibody is a single-chain fragment, a Fab fragment, or a pair of Fab fragments. In some embodiments, the anti-PD-L1 antibody is a monospecific antibody or a bispecific antibody that further has a second specificity. In some embodiments, the anti-PD-L1 antibody is ADCC-enabled.

In some embodiments, the anti-PD-L1 antibody or the antigen-binding fragment thereof comprises a heavy chain variable region comprising CDR1, CDR2, and CDR3 having the amino acid sequences of residues 31-35, residues 50-66, and residues 99-108 of SEQ ID NO:6 respectively, and a light chain variable region comprising CDR1, CDR2, and CDR3 having the amino acid sequences of residues 24-34, residues 50-56, and residues 89-97 of SEQ ID NO:7 respectively. In some embodiments, the anti-PD-L1 antibody or the fragment thereof comprises a heavy chain variable region comprising the amino acid sequence of SEQ ID NO: 6, and a light chain variable region comprising the amino acid sequence of SEQ ID NO: 7.

In some embodiments, the IL-7 protein comprises the amino acid sequence of SEQ ID NO: 9 or an amino acid sequence having at least 95% sequence identity to SEQ ID NO: 9 while capable of binding IL-7 receptor alpha. In some embodiments, the IL-7 protein has an amino acid residue selected from Gly, Ala, Val, Cyc, Leu, Ile, Met, and Phe at position 142 according to SEQ ID NO:9. In some embodiments, the IL-7 protein has an amino acid residue selected from A, V, L, I, M, and F at position 142 according to SEQ ID NO:9. In some embodiments, the amino acid sequence having at least 95% sequence identity to SEQ ID NO: 9 has reduced binding affinity to the IL-7 receptor alpha as compared to the wild-type human IL-7 protein. In some embodiments, the IL-7 protein comprises the amino acid sequence of SEQ ID NO: 9. In some embodiments, a fragment of the IL-7 protein is included in the fusion molecule. In some embodiments, the fragment includes at least one, two, three or all four alpha-helix motifs.

In some embodiments, peptide linker is fused to the C-terminal residue of the PD-L1 inhibitor, and fused to the N-terminal residue of the IL-7 protein. In some embodiments, the peptide linker is fused to the N-terminal residue of the PD-L1 inhibitor, and fused to the C-terminal residue of the IL-7 protein. In some embodiments, the peptide linker is fused to the N-terminal residue of a light chain of the anti-PD-L1 antibody or fragment thereof. In some embodiments, the peptide linker is fused to the N-terminal residue of a heavy chain of the anti-PD-L1 antibody or fragment thereof.

Also provided, in one embodiment, is an isolated protein, comprising the amino acid sequence of SEQ ID NO: 9 or a peptide having at least 95% sequence identity to SEQ ID NO: 9, wherein the peptide is capable of binding IL-7 receptor alpha but has reduced binding affinity to the IL-7 receptor alpha as compared to the wild-type human IL-7 protein. In some embodiments, the peptide has an amino acid residue other than Trp at location 142. In some embodiments, the peptide has, at location 142, an amino acid residue selected from the group consisting of Ala, Gly, Cys, Leu, Ile, Met, Phe, and Val. In some embodiments, the peptide has, at location 142, an amino acid residue selected from the group consisting of Ala, Leu, Ile, Met, Phe, and Val.

Methods of treating a cancer are also provided, in a patient in need thereof. In some embodiments, the method entails administering to the patient a molecule of the present disclosure. In some embodiments, the method entails administering an IL-7 variant as disclosed, optionally with a PD-L1 inhibitor. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

DETAILED DESCRIPTION

Definitions

Figure 1:
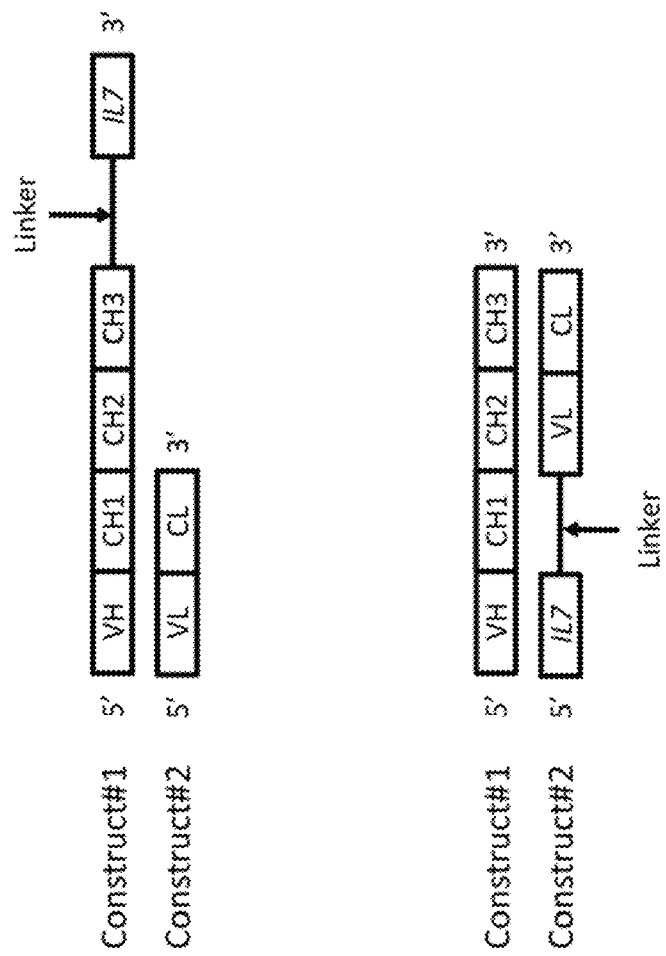
FIG. 1, in panels A-D, illustrate a few fusion molecule structures.
Figure 1:
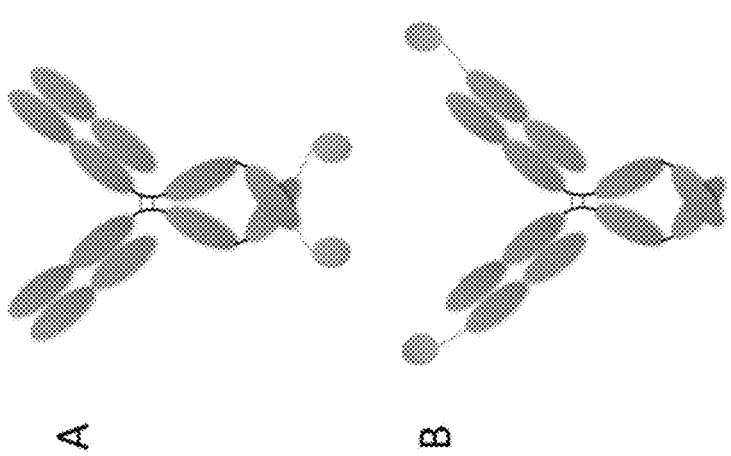
Figure 1:
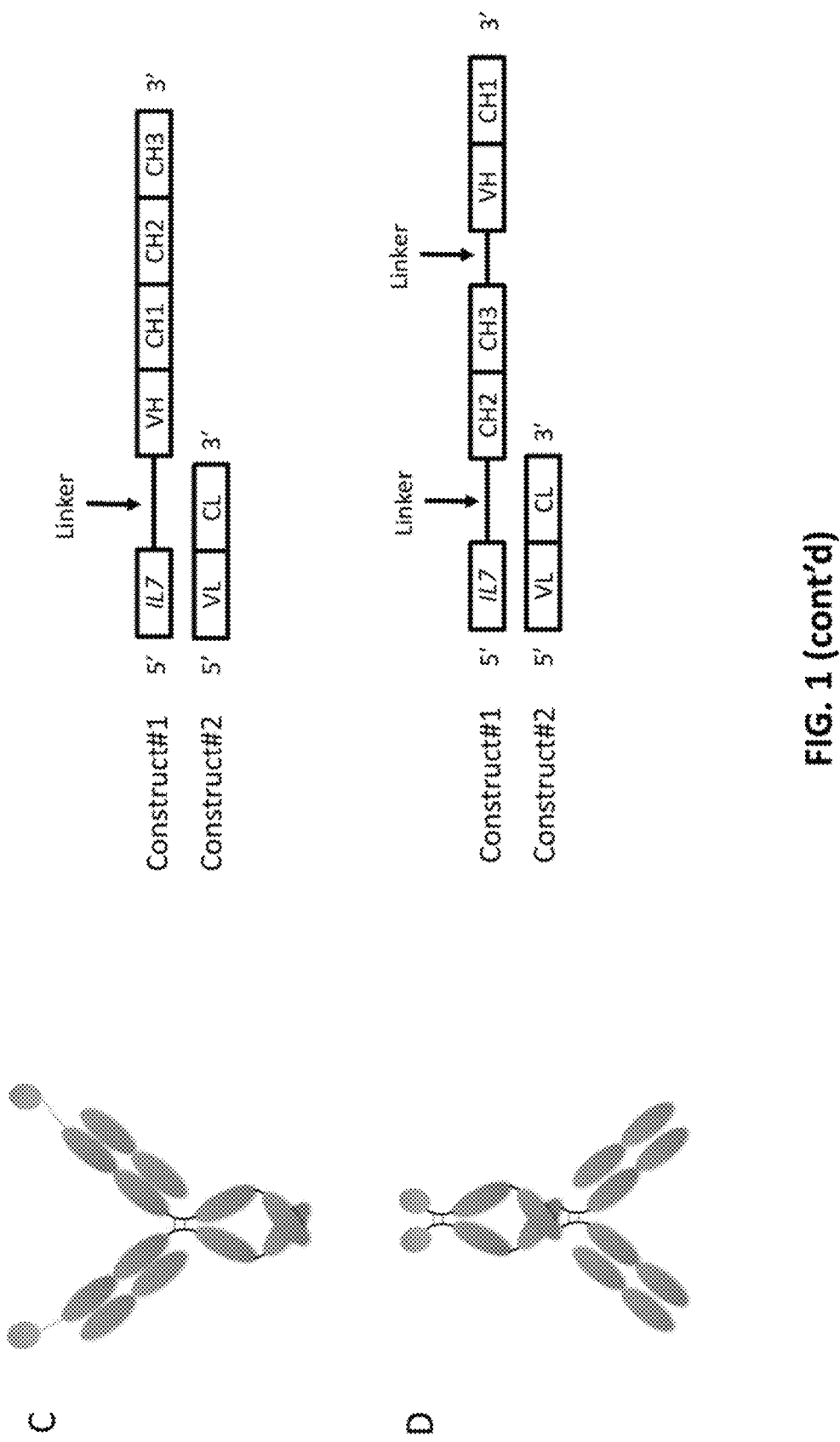

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains (V_L) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (К, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an IgG3 molecule. In another example, a heavy chain portion can comprise a chimeric hinge derived, in part, from an $IgG_1$ molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Fusion Molecules

The present disclosure provides fusion molecules that combine PD-L1 inhibition or blockade with an IL-7 cytokine activity in a synergistic manner which further maximizes efficacy and safety.

In one embodiment, the fusion molecule includes a PD-L1 inhibitor (e.g., a decoy PD-1 protein or an anti-PD-L1 antibody or fragment thereof) fused to a human IL-7 protein or fragment thereof, preferably through a peptide linker. The peptide linker is generally a peptide that has from 5 to 100 amino acid residues. Preferably, the linker includes enough smaller amino acids to ensure its flexibility. For instance, the length of the linker can be from 5 to 100 amino acids, from 10 to 90 amino acids, from 10 to 80 amino acids, from 10 to 75 amino acids, from 15 to 90 amino acids, from 15 to 80 amino acids, from 15 to 70 amino acids, from 20 to 80 amino acids, from 20 to 70 amino acids, from 20 to 60 amino acids, from 25 to 90 amino acids, from 25 to 80 amino acids, from 25 to 75 amino acids, from 25 to 70 amino acids, from 25 to 60 amino acids, from 30 to 80 amino acids, from 30 to 70 amino acids, from 30 to 60 amino acids, or from 40 to 70 amino acids, without limitation.

The flexibility of the linker can be achieved by incorporating a minimum percentage of smaller amino acids, e.g., alanine, glycine, cysteine, and serine. In some embodiment, the linker includes at least 10%, 15%, 20%, 25%, 30%, 35%, 40%, 45%, 50%, 55%, 60%, 65%, 70%, 75% or 80% of amino acids selected from alanine, glycine, cysteine, or serine. Non-limiting examples of peptide linkers are provided in SEQ ID NO: 1-5.

The human IL-7 protein is known, with a protein sequence deposited in GenBank at accession no. NP_000871.1, of which the mature sequence is provided in SEQ ID NO: 8. Through calculation and testing, it was determined that mutant forms of the IL-7 protein with reduced IL-7 activity maintained synergism with the anti-PD-L1 antibody as compared to the wild-type IL7, with overall improved safety. Non-limiting examples of such mutants include those having an amino acid substitution at $IL7^{W142}$. The substitution can be with a non-polar amino acid such as G, A, V, C, P, L, I, M, and F.

The term "human IL-7 protein" as used herein refers to the wild-type human IL-7 as well as its biological equivalents, i.e., those that have at least 75%, 80%, 85%, 90%, 95%, 98%, or 99% sequence identity to the wild-type human IL-7 and maintain the activity of the wild-type such as binding to an IL-7 receptor (e.g., receptor alpha), which can be readily measured. In some embodiments, the human IL-7 protein has reduced IL-7 activity as compared to the wild-type. In some embodiments, the reduced IL-7 activity is at least 20%, 30%, 40%, 50%, 60%, 70%, 80% or 90% of binding activity to IL-7 receptor as compared to the wild-type IL-7. In some embodiments, the IL-7 activity is at least 1%, 2%, 5%, 10%, 15%, 20%, 30%, 40%, 50%, 60%, 70%, 80%, 90%, 95%, 97%, 98%, 98%, 99%, 99.9%, 99.99%, 99.999%, 99.9999% lower than that of the wild-type IL-7. In some embodiments, the IL-7 activity is between that of $IL-7^{W142A}$ and wild-type IL-7. In some embodiments, the IL-7 protein is a synthetic analog that is capable of binding to an IL-7 receptor.

In some embodiments, the human IL-7 protein includes a mutation at W142 as compared to the wild-type. In some embodiments, the mutation is to a non-polar amino acid. Non-limiting examples of the mutation include a mutation to Ala, Gly, Cys, Leu, Ile, Met, Phe, or Val. In some embodiments, the mutation is to Phe, Met, Ile, Leu, Val, or Ala. In a preferred embodiment, the mutation is W142A (e.g., SEQ ID NO: 9).

A fragment of the IL-7 protein can also be used, in some embodiments. The fragment, in some embodiments, is capable of binding an IL-7 receptor (e.g., receptor alpha), preferably with reduced IL-7 activity as compared to the wild-type protein. The 3-dimensional structures of IL-7 in complex with IL-7 receptors have been demonstrated. See, e.g., McElroy et al., Structure. 2009 Jan. 14; 17(1):54-65. IL-7 adopts an up-up-down-down 4-helix bundle topology with two crossover loops. The α-helices A-D vary in length from 13 to 22 residues. In some embodiments, the fragment includes at least one, two, or three of the alpha helices. In some embodiments, the fragment includes all four of the alpha helices. In some embodiments, the fragment retains interface amino acid residues including S19, D74 and K81.

The IL-7 protein can allow further modifications, such as addition, deletion and/or substitutions, at other amino acid locations as well. Such modifications can be substitution at one, two or three positions. In one embodiment, the modification is substitution at one of the positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

As used herein, the term "PD-L1 inhibitor" refers to a molecule, e.g., a protein or a protein-containing complex, that is able to bind to PD-L1 and block interaction between PD-1 and PD-L1 and thus inhibit the activity of PD-L1. A non-limiting example of a PD-L1 inhibitor is a decoy PD-1 protein, e.g., an inactive PD-1 variant that maintains the ability to bind PD-L1. Examples of such PD-1 variants are provided in Maute et al., "Engineering high-affinity PD-1 variants for optimized immunotherapy and immuno-PET imaging,"*PNAS* 2015 112 (47) E6506-E6514 (2015). Another non-limiting example is an anti-PD-L1 antibody.

There are many known anti-PD-L1 antibodies and their fragments that are suitable for inclusion in the fusion molecules of the present disclosure. The sequences of heavy chain variable region and light chain variable region are provided in SEQ ID NO: 6 and 7 for an example anti-PD-L1 antibody. Variant anti-PD-L1 antibodies that include the CDR regions of the example antibody are also within the scope of the present technology. For instance, the anti-PD-L1 antibody or the antigen-binding fragment thereof can include a heavy chain variable region comprising CDR1,

TABLE A

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

CDR2, and CDR3 having the amino acid sequences of residues 31-35, residues 50-66, and residues 99-108 of SEQ ID NO:6 respectively, and a light chain variable region comprising CDR1, CDR2, and CDR3 having the amino acid sequences of residues 24-34, residues 50-56, and residues 89-97 of SEQ ID NO:7 respectively.

In some embodiments, the anti-PD-L1 antibody is of an isotype of IgG, IgM, IgA, IgE or IgD, and the fragment can take any form, such as a single-chain fragment, a Fab fragment, or a pair of Fab fragments. In some embodiments, the anti-PD-L1 antibody is ADCC-enabled.

Some example structures of the fusion molecules are illustrated in FIG. 1, panels A-D. In panel A, the fusion molecule includes a full IgG anti-PD-L1 antibody and two IL-7 proteins each fused, through a linker, to the C-terminus of CH3 of the antibody. This fusion polypeptide can be made with two separate DNA constructs. In panel B, the fusion molecule also includes an IgG anti-PD-L1 antibody and two IL-7 proteins; however, the IL-7 proteins are fused, through a linker, to the N-terminus of the light chains variable regions.

In FIG. 1, panel C, different that in panel C, the IL-7 proteins are fused, through the linkers, to the N-terminus of the heavy chain. Another example structure is illustrated in panel D, which shows each IL-7 protein fused through a linker to the N-terminus of CH2 of the antibody in which the CH2-CH3 fragment is placed upstream of the VH-CH2 portion.

Still more structures, which are not illustrated in the figures, can be made, which could be a monospecific antibody or a bispecific antibody that further has a second specificity.

In certain embodiments, the decoy PD-1 protein or antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the decoy PD-1 proteins or antibodies may be conjugated to therapeutic agents, prodrugs, peptides, proteins, enzymes, viruses, lipids, biological response modifiers, pharmaceutical agents, or PEG.

The decoy PD-1 proteins or antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The decoy PD-1 proteins or antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The decoy PD-1 proteins or antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

IL-7 Variants

Mutants of the human IL-7 protein were prepared that have reduced activity as compared to the wild-type protein. These mutants are proven to be useful in situations where such reduction of activity is desired, e.g., for safety concerns. Accordingly, in one embodiment, the present disclosure also provides isolated polypeptide that includes such mutants.

In some embodiments, the present disclosure provides an isolated polypeptide that includes the amino acid sequence of SEQ ID NO: 9. In some embodiments, the polypeptide includes a peptide having at least 75%, 80%, 85%, 90%, 95%, 98%, or 99% sequence identity to SEQ ID NO: 9, wherein the peptide is capable of binding IL-7 receptor alpha but has reduced binding affinity to the IL-7 receptor alpha as compared to the wild-type human IL-7 protein.

In some embodiments, the human IL-7 protein has reduced IL-7 activity as compared to the wild-type. In some embodiments, the reduction of IL-7 activity is at least 20%, 30%, 40%, 50%, 60%, 70%, 80% or 90% of binding activity to IL-7 receptor.

In some embodiments, the human IL-7 protein includes a mutation at W142 as compared to the wild-type. In some embodiments, the mutation is to a non-polar amino acid. Non-limiting examples of the mutation include mutation to Ala, Gly, Cys, Leu, Ile, Met, Phe, or Val. In some embodiments, the mutation is to Phe, Met, Ile, Leu, Val, or Ala. In a preferred embodiment, the mutation is W142A. In some embodiments, the mutation at W142 is selected from Gly, Cys, Leu, Ile, Met, Phe, or Val.

A fragment of the IL-7 protein can also be used, in some embodiments. The fragment, in some embodiments, is capable of binding an IL-7 receptor (e.g., receptor alpha), preferably with reduced IL-7 activity as compared to the wild-type protein. In some embodiments, the fragment includes at least one, two, or three of the alpha helices. In some embodiments, the fragment includes all four of the alpha helices. In some embodiments, the fragment retains interface amino acid residues including S19, D74 and K81.

The IL-7 protein can allow further modifications, such as addition, deletion and/or substitutions, at other amino acid locations as well. Such modifications can be substitution at one, two or three positions. In one embodiment, the modification is substitution at one of the positions. Such substitutions, in some embodiments, are conservative substitutions.

Polynucleotides Encoding the Polypeptides and Methods of Preparing the Polypeptides The present disclosure also provides isolated polynucleotides or nucleic acid molecules encoding the decoy PD-1 proteins, antibodies, fusion molecules, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making decoy proteins and antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As demonstrated herein, the fusion molecules of the present disclosure exhibited synergistic effects in treating cancer, and may be used in certain treatment and diagnostic methods.

The present disclosure is further directed to therapies which involve administering the fusion molecules of the disclosure to a patient such as an animal, a mammal, and a human for treating one or more of the disorders or conditions described herein. Therapeutic compounds of the disclosure include, but are not limited to, fusion molecules of the disclosure (including variants and derivatives thereof as described herein) and nucleic acids or polynucleotides encoding fusion molecules of the disclosure (including variants and derivatives thereof as described herein).

The therapy can also involve administering IL-7 variants as disclosed herein, optionally in combination with administration of a PD-L1 inhibitor as disclosed herein. In some embodiments, the IL-7 variant administered and the PD-L1 inhibitor administered have a molar ratio that is at least 5:1, 4:1, 3:1, 2:1, 1.5:1, 1:1, or 1:2. In some embodiments, the IL-7 variant administered and the PD-L1 inhibitor administered have a molar ratio that is not greater than 2:1, 1.5:1, 1:1, 1:2, 1:3, 1:4, or 1:5. In some embodiments, the IL-7 variant administered and the PD-L1 inhibitor administered have a molar ratio between 2:1 and 1:2 or between 1.5:1 and 1:1.5.

Cellular therapies, such as chimeric antigen receptor (CAR) T-cell therapies, are also provided in the present disclosure. A suitable cell can be used, that is put in contact with an anti-PD-L1 antibody of the present disclosure (or alternatively engineered to express an anti-PD-L1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the fusion molecules or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular fusion molecules, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the fusion molecules, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the fusion molecules of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the fusion molecules or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the fusion molecules of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of fusion molecules of the disclosure may be reduced by enhancing uptake and tissue penetration (e.g., into the brain) of the fusion molecules by modifications such as, for example, lipidation.

Compositions

The present disclosure also provides pharmaceutical compositions. Such compositions comprise an effective amount of a fusion molecule, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1: Design and Generation of Anti-PDL1 and Human IL7 Fusion Molecules The heavy chain or light chain gene of an anti-PDL1 antibody (see variable region sequences in Table 1) was designed to fuse with human IL7 gene (Table 2) with peptide linkers in Table 3. The resulting genes were then cloned into mammalian expression vectors and transfected into HEK293T cells. The antibody-cytokine fusion proteins (structure in FIG. 1, panel A) were purified by protein A from the supernatants of transfected cells.

Example 2: IL7 Cytokine Potency of Anti-PDL1-IL7 Fusion Molecules

All anti-PDL1-IL7 fusion molecules in the examples below used Format A in FIG. 1. These bi-functional molecules combined PDL1 antagonism with IL7 cellular activity. Given the fixed mole ratio (1:1) of anti-PDL1 molecule and IL7, it was contemplated that IL7 variants with a different activity level might have better synergism with the anti-PDL1 function.

Figure 2:
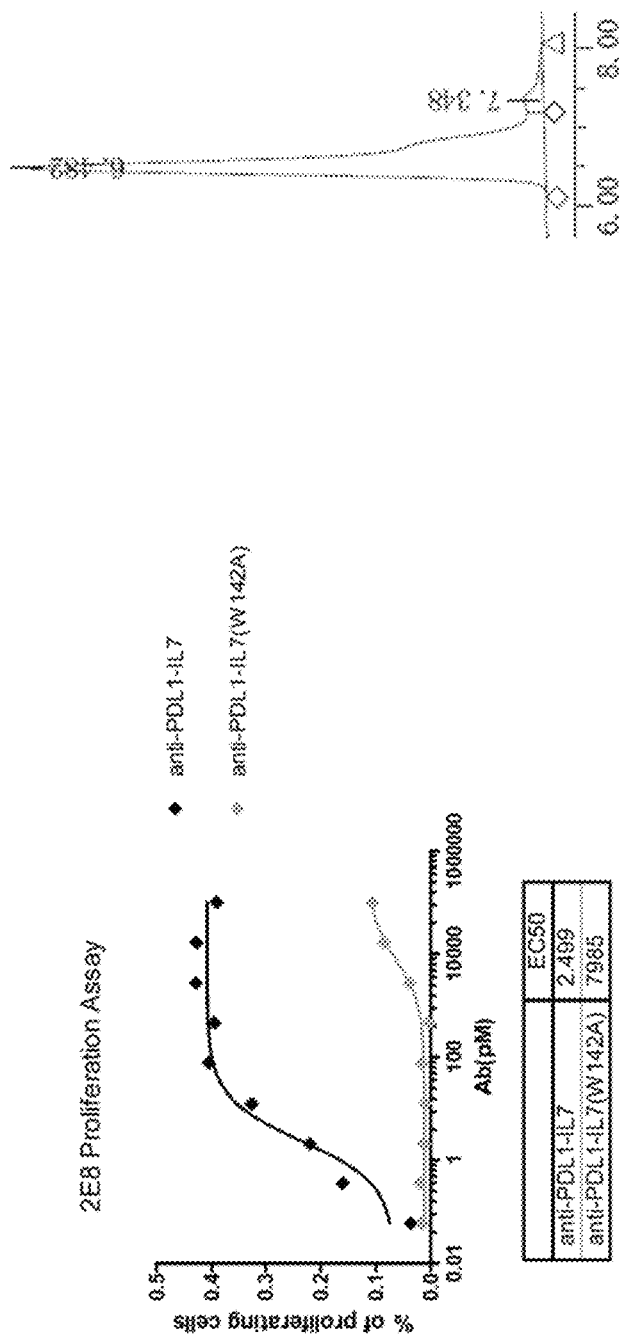
FIG. 2 shows the identification of the W142A mutation that reduces the IL-7 protein activity.

The crystal structure of IL7/IL7R have been resolved (Structure 2009, 17: 54-65). The data have shown that amino acids K120, R133, L135, Q136, E137, K139, T140, W142, N143 and K144 are at the interface of IL7 and common γ chain (IL7 signal transduction receptor) (FIG. 2). Each of these 10 amino acids was mutated to Ala and evaluated with respect to purity by SEC-HPLC and IL7 activity by 2E8 cell proliferation assay (IL7 can drive the proliferation of 2E8

TABLE 1

Anti-PD-L1 Antibody Sequences (CDR residues underlined)

| Name | Sequence | SEQ ID NO: |
|---|---|---|
| Heavy chain variable | EVQLVESGGG LVQPGGSLRL SCAASGFTFS SYDMSWVRQA PGKSLEWVAT ISDAGGYIYY SDSVKGRFTI SRDNAKNSLY LQMNSLRDED TAVYICAREF GKRYALDYWG QGTTVTVSS | 6 |
| Light chain variable | DIQMTQSPSS LSASVGDRVT ITCKASQDVT PAVAWYQQKP GKAPKLLIYS TSSRYTGVPS RFSGSGSGTD FTFTISSLQP EDIATYYCQQ HYTTPLTFGQ GTKLEIK | 7 |

TABLE 2

IL-7 Sequences

| Name | Sequence (underlined bold letter indicates mutation) | SEQ ID NO: |
|---|---|---|
| Human IL-7 | DCDIEGKDGK QYESVLMVSI DQLLDSMKEI GSNCLNNEFN FFKRHICDAN KEGMFLFRAA RKLRQFLKMN STGDFDLHLL KVSEGTTILL NCTGQVKGRK PAALGEAQPT KSLEENKSLK EQKKLNDLCF LKRLLQEIKT CWNKILMGTK EH | 8 |
| Human IL-7 W142A mutant | DCDIEGKDGK QYESVLMVSI DQLLDSMKEI GSNCLNNEFN FFKRHICDAN KEGMFLFRAA RKLRQFLKMN STGDFDLHLL KVSEGTTILL NCTGQVKGRK PAALGEAQPT KSLEENKSLK EQKKLNDLCF LKRLLQEIKT CANKILMGTK EH | 9 |

TABLE 3

Peptide linker sequences

| Linker No. | Sequence | SEQ ID NO: |
|---|---|---|
| 1 | GGGGSGGGGS | 1 |
| 2 | GGGGSGGGGS GGGGS | 2 |
| 3 | GGGGSGGGGS GGGGSGGGGS GGGGSGGGGS | 3 |
| 4 | GSGSGSGSGS GSGSGSGS | 4 |
| 5 | EPKSSDKTHT CPPCP | 5 | cells). Mutant W142A showed significantly reduced IL7 potency and excellent purity as shown in FIG. 2.

Figure 3:
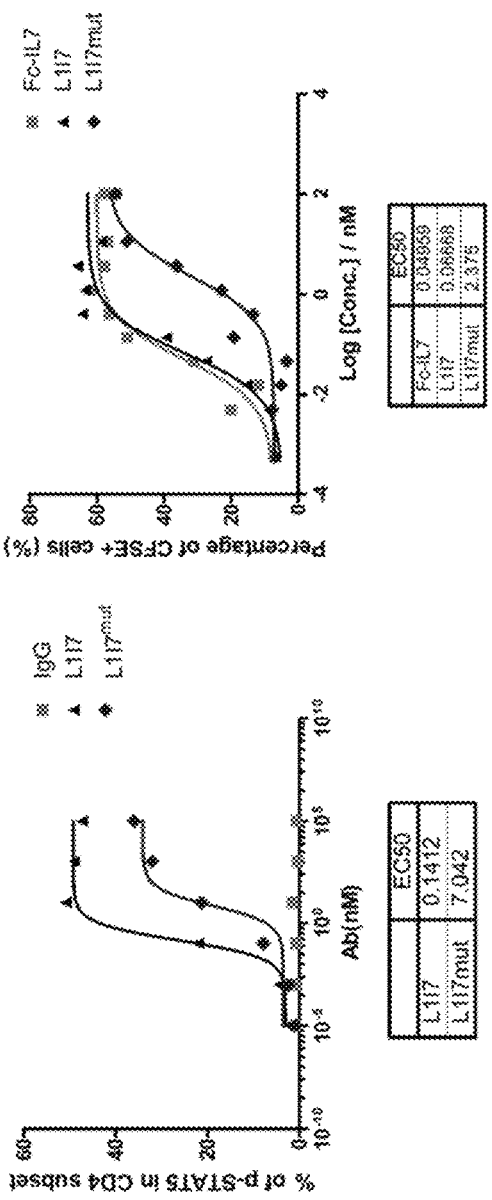
FIG. 3 demonstrates that the W142A mutation indeed reduced the IL7 potency of anti-PDL1-IL7 fusion molecules.
Figure 4A:
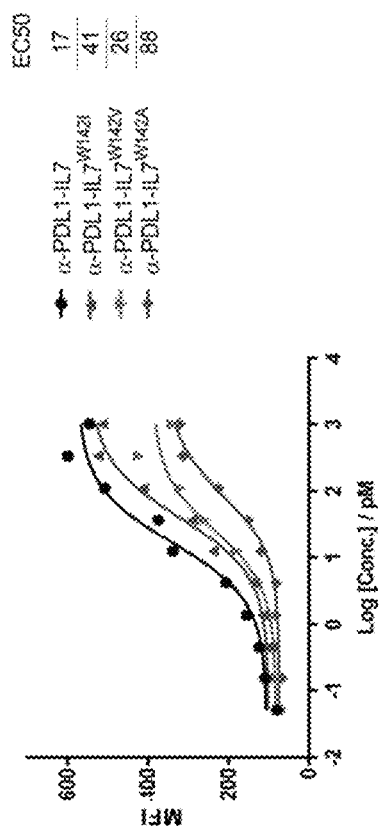
FIG. 4, with panels A-C, presents results of the fusion molecules' ability to stimulate STAT5 signaling (A), to bind IL7R (B), and to promote IL7R internalization (C).
Figure 4C:
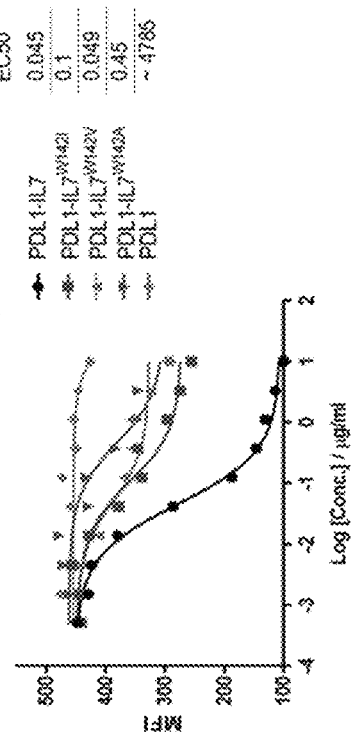
Figure 4B:
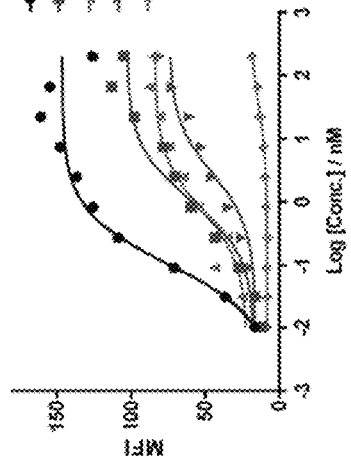
Figure 5:
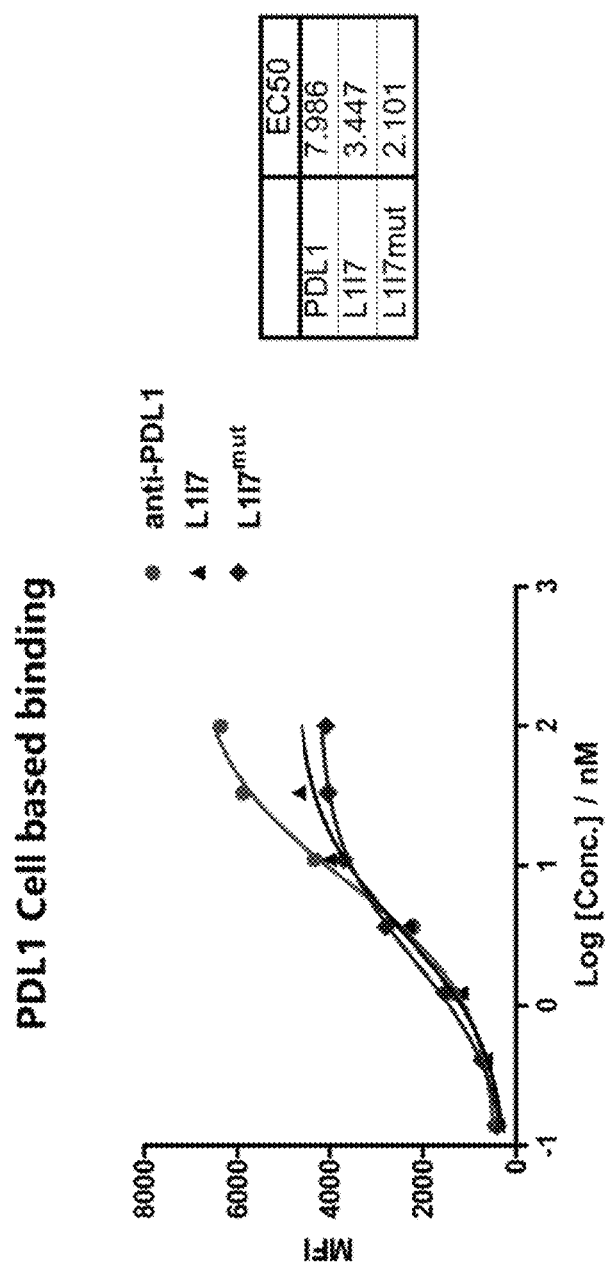
FIG. 5 shows the fusion molecule's ability to bind to cell-bound PDL1 protein.

Because IL7 can induce the STAT5 phosphorylation (pSTAT5) and later on proliferation of CD4 T cells, to further evaluate the IL-7 potency of wild-type (WT) and W142A IL7 on primary human T cells, the pSTAT5 assay and CD4 proliferation assay were performed. Briefly, in pSTAT5 assay, human PBMCs were treated with anti-PDL1-IL7 and anti-PDL1-IL7$^{W142A}$ at the indicated concentration for 15 min. In CD4 proliferation assay, the purified CD4 T cells were treated with anti-PDL1-IL7 and anti-PDL1-IL7$^{W142A}$ for 1 week. As shown in FIG. 3, the W142A mutation indeed reduced the IL7 potency of anti-PDL1-IL7 fusion molecules.

To fine tune IL7 activity of anti-PDL1-IL7 fusion molecule, a series of single site mutations on W142 of IL7 were generated. Based on the polarity, numbers of amino and hydroxyl, the 20 amino acids can be divided into four categories: non-polar (G, A, V, C, P, L, I, M, W and F), polar (S, T, Y, N and Q), positively charged (K, R and H) and negatively charged (D and E) groups. A few representative amino acids from each group were selected to construct mutant anti-PDL1-IL7 molecules as described below (Table 4). It was shown that all of the non-polar amino acids except Proline (P) can substitute with W142 to generate mutant anti-PDL1-IL7 with high SEC purity (>96.8%). On the contrary, mutation of W142 to other three types of amino acids caused reduced molecule stability and SEC purity (<84%). Next, each amino acid within the non-polar amino acid subtypes was used to replace W to generate a series of mutant anti-PDL1-IL7 molecules to perform IL7 activity validation by 2E8 proliferation assay (Table 5). It was shown that the less similarity the substitute amino acid had with W, the lower IL7 activity the mutated molecule had (W>F>M>I>L>V>A).

To confirm the attenuation of IL7 activity of the anti-PDL1-IL7 mutant molecules in primary $CD4^+$ T cells, p-STATS signaling assay was performed as above. As shown in FIG. 4A, the ability of fusion molecules to stimulate STATS signaling in human primary $CD4^+$ T cells gradually decreased (W>I>V>A), which correlated with their corresponding activity in 2E8 proliferation assay. In order to explain the mechanism of attenuated IL7 activities of the serial mutant anti-PDL1-IL7 molecules, IL7 receptor (IL7R) binding and ligation-mediated internalization were evaluated. Briefly, for IL7R binding assay, human primary $CD4^+$ T cells were incubated with various anti-PDL1-IL7 fusion molecules at 4° C. for 30 mins. PE-conjugated anti-human Fc secondary antibody were used to detect the fusion molecules that bound to the IL7R of $CD4^+$ T cells by FACS. As shown in FIG. 4B, all of the three anti-PDL1-IL7 fusion molecules (W142I, V and A) with decreased IL7 activities had reduced IL7R binding. For ligation-mediated receptor internalization assay, human primary $CD4^+$ T cells were cocultured with fusion molecules at 37° C. for 15 mins. PE-cy7-conjugated-anti-CD127 (IL7Ra) antibody was used to detect the surface IL7R by FACS. Similar to the trends of IL7R binding, those fusion molecules with reduced IL7 receptor binding potency had compromised IL7R internalization (FIG. 4C), indicating impaired IL7 signaling transduction. In conclusion, we have developed a series of anti-PDL1-IL7 molecules with different and attenuated IL7 activities by modifying a single site mutation of W142.

TABLE 4

Comparison of SEC property of various PDL1-IL7 mutants

| Classification of amino acids | Protein | Expression (mg/L) | SEC % |
|---|---|---|---|
| Wild type | anti-PDL1-IL7 | 4 | 99.90 |
| Non-polar | anti-PDL1-IL7$^{W142A}$ | 2.9 | 97.80 |
| | anti-PDL1-IL7$^{W142I}$ | 3.9 | 99.20 |
| | anti-PDL1-IL7$^{W142M}$ | 2.7 | 96.80 |
| | anti-PDL1-IL7$^{W142P}$ | 1.9 | 52.00 |
| Positive charge | anti-PDL1-IL7$^{W142R}$ | 2.8 | 39.00 |
| Negative charge | anti-PDL1-IL7$^{W142D}$ | 2.1 | 54.00 |
| Polar | anti-PDL1-IL7$^{W142S}$ | 3.2 | 84.00 |
| | anti-PDL1-IL7$^{W142Q}$ | 2.6 | 64.00 |

TABLE 5

Comparison of EC50 of various PDL1-IL7 mutants in 2E8 proliferation assay

| | Protein | Fold change of EC50 in 2E8 proliferation assay ($EC50_{Mutant}/EC50_{WT}$) |
|---|---|---|
| 1 | anti-PDL1-IL7 | 1 |
| 2 | anti-PDL1-IL7$^{W142F}$ | 1.5 |
| 3 | anti-PDL1-IL7$^{W142M}$ | 5.3 |
| 4 | anti-PDL1-IL7$^{W142I}$ | 10.1 |
| 5 | anti-PDL1-IL7$^{W142L}$ | 96.1 |
| 6 | anti-PDL1-IL7$^{W142V}$ | 346.7 |
| 7 | anti-PDL1-IL7$^{W142A}$ | 4840.4 |

Example 3: PDL1 Binding Properties of Anti-PDL1-IL7 Fusion Molecules

This example examined the full kinetic affinity of humanized antibodies by Biacore®.

The binding of the anti-PDL1-IL7 fusion molecule to recombinant PD-L1 protein (human PD-L1-his taq) was tested by BIACORE® using a capture method. The anti-PDL1-IL7 fusion molecules was captured using anti-human Fc antibody coated on a CM5 chip. A series of dilutions of human PD-L1-his taq protein were injected over captured antibody for 3 mins at a flow rate of 25 μg/ml. The antigen was allowed to dissociate for 900 s. All the experiments were carried out on a Biacore T200. Data analysis was carried out using Biacore T200 evaluation software. The data show that the PDL1 binding affinity was not compromised in the fusion molecules (Table 6).

TABLE 6

Affinity testing results

| Sample | ka (1/Ms) | kd (1/s) | KD (M) |
|---|---|---|---|
| Anti-PDL1 mAb | 8.50E+04 | 1.78E−04 | 2.09E−09 |
| anti-PDL1-IL7 | 1.03E+05 | 2.78E−04 | 2.70E−09 |
| anti-PDL1-IL7$^{W142V}$ | 8.20E+04 | 4.15E−04 | 5.06E−09 |

To evaluate the antigen binding property, the fusion molecules were analyzed for their binding to mammalian expressed PD-L1 by FACS. Briefly, PDL1-Raji cells were first incubated with 3-fold serious diluted humanized antibodies starting at 15 μg/ml at RT for 1 hour. After washing by FACS buffer (PBS with 2% FBS), the Alexa 488-anti-human IgG antibody was added to each well and incubated at RT for 1 hour. The MFI of Alexa 488 were evaluated by FACSAriaIII. As shown in FIG. 5, all the fusion molecules showed similar binding to anti-PDL1 monoclonal antibody.

Example 4: PDL1 Antagonist Activity of Anti-PDL1-IL7 Fusion Molecules

To evaluate the PDL1 antagonist, PD1/PDL1 Jurkat assays were performed. Super antigen Staphylococcal Enterotoxin (SEE) stimulated the IL2 production by Jurkat T cells in the presence of Raji cells through ligation of MHCII on Raji and TCR molecules on Jurkat. PDL1 exogenous expressed on Raji cells bound to PD1 overexpressed by Jurkat T cells and inhibited the IL2 production by Jurkat. The anti-PDL1 monoclonal antibody (mAb) reversed IL2 production suppressed by PD1/PDL1 pathway. As shown in

Figure 6:
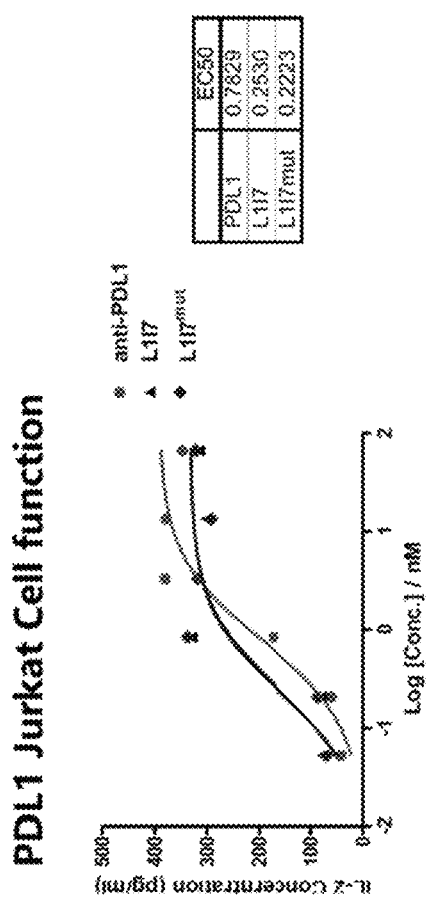
FIG. 6 shows that all tested fusion molecules showed similar binding to anti-PDL1 monoclonal antibody.
Figure 6:
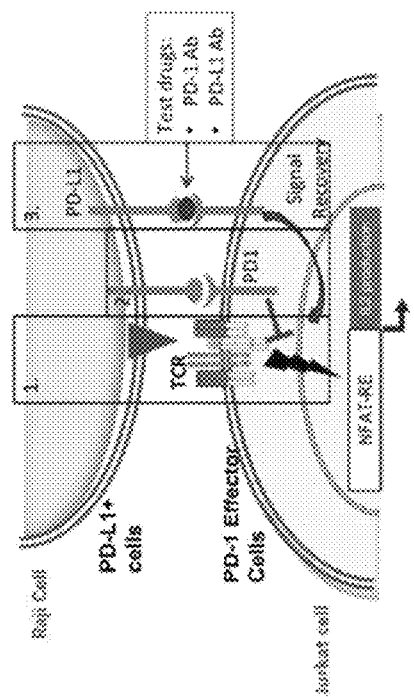

FIG. 6, anti-PDL1-IL7 and anti-PDL1-IL7$^{W142A}$ fusion molecules showed comparable PDL1 antagonist function with anti-PDL1 mAb.

Example 5: The Bi-Specific Binding of Anti-PDL1-IL7 Fusion Molecules

Figure 7:
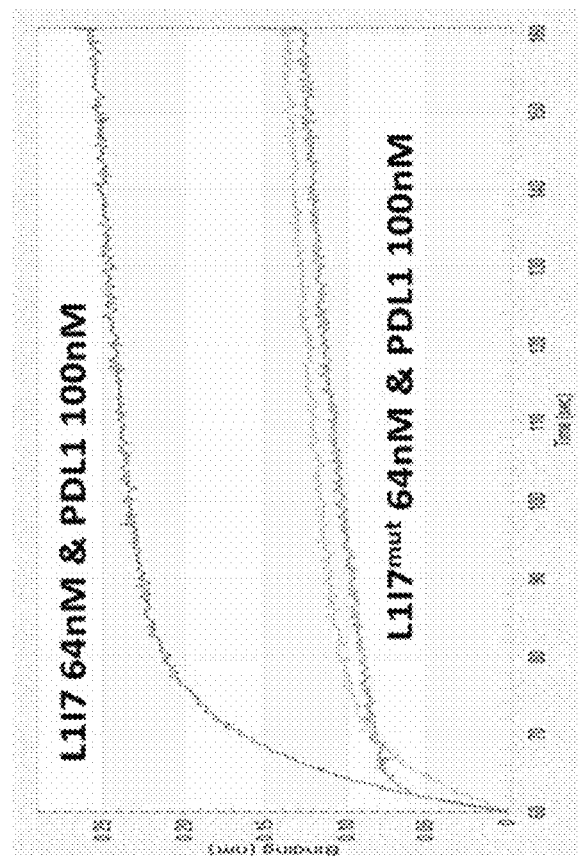
FIG. 7 shows that anti-PDL1-IL7$^{W142A}$ had reduced binding to IL7Ra, which was consistent with its reduced IL7 potency.
Figure 7:
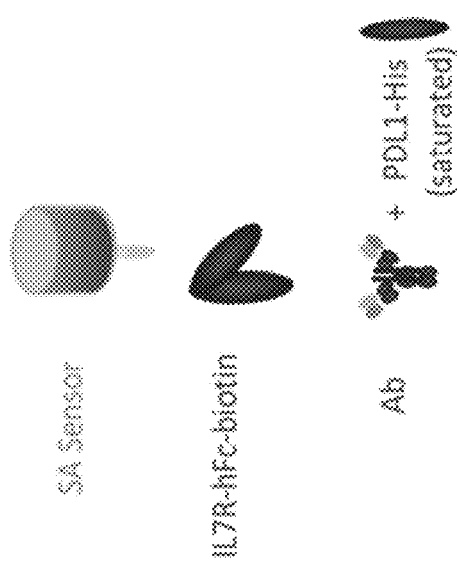

To verify the fusion molecules with bi-specific binding properties with PDL1 and IL7 receptor alpha (IL7Ra), this example used Bio-Layer Interferometry (BLI) measuring the bi-specific bindings. Briefly, biotin-labeled IL7Ra was firstly captured by streptavidin sensor. The anti-PDL1-IL7 fusion molecule was captured by IL7Ra. The saturated concentration (100 nM) of his-PDL1 was used to evaluated PDL1 binding. All the fusion molecules showed bi-specific binding of PDL1 and IL7Ra (FIG. 7). In addition, anti-PDL1-IL7$^{W142A}$ showed reduced binding to IL7Ra, which was consistent with its reduced IL7 potency (FIG. 7).

Example 6: Synergistic Stimulation of Anti-PDL1-IL7 Fusion Molecule on Human T Cell Function To evaluate the in vitro function of fusion molecules, the response of human T cells was assessed in a mixed lymphocyte reaction setting. Human DCs were differentiated from CD14+ monocytes in the presence of GM-CSF and IL-4 for 7 days. CD4$^+$ T cells isolated from another donor were then co-cultured with the DCs and serial dilutions of fusion molecules.

Figure 8:
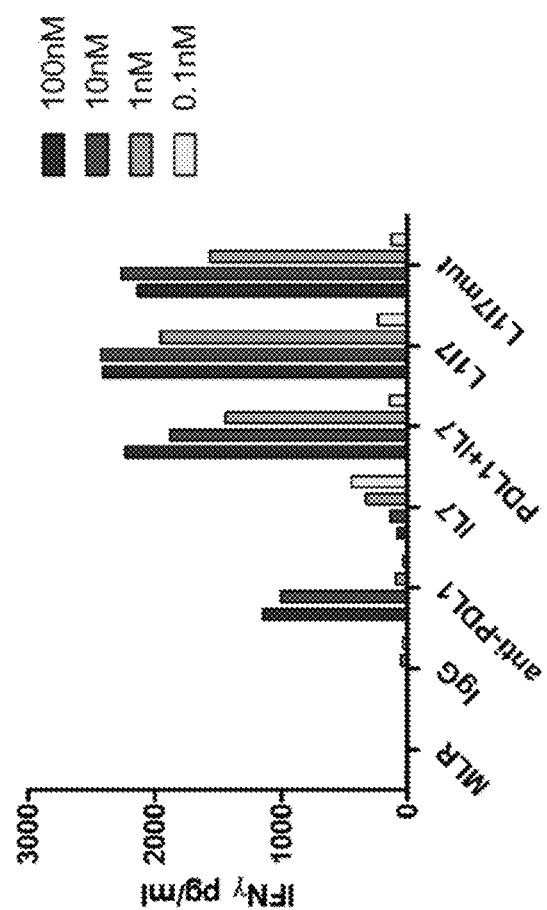
FIG. 8 shows that anti-PDL1-IL7 and anti-PDL1-IL7$^{W142A}$ had superior efficacy than anti-PDL1 mAb or IL7 on enhancing human T cell function.

At day 5 post-inoculation, the culture supernatant was assayed for IFNγ production. The results indicated anti-PDL1-IL7 and anti-PDL1-IL7$^{W142A}$ showed superior efficacy than anti-PDL1 mAb or IL7 on enhancing human T cell function (FIG. 8). Anti-PDL1-IL7$^{W142A}$ with reduced IL7 potency, showed comparable potency as L117 on human T cell response. Therefore, fusion molecules had synergistic effect of PDL1 antagonism and IL7 effect and full IL7 activity as not necessary for the synergistic effect. The anti-PDL1-IL7 molecules with reduced IL7 activity and strong synergistic effect on immune-stimulation may have better safety profile in the future clinics.

Example 7: In Vivo Tracking of Anti-PDL1-IL7

Figure 9:
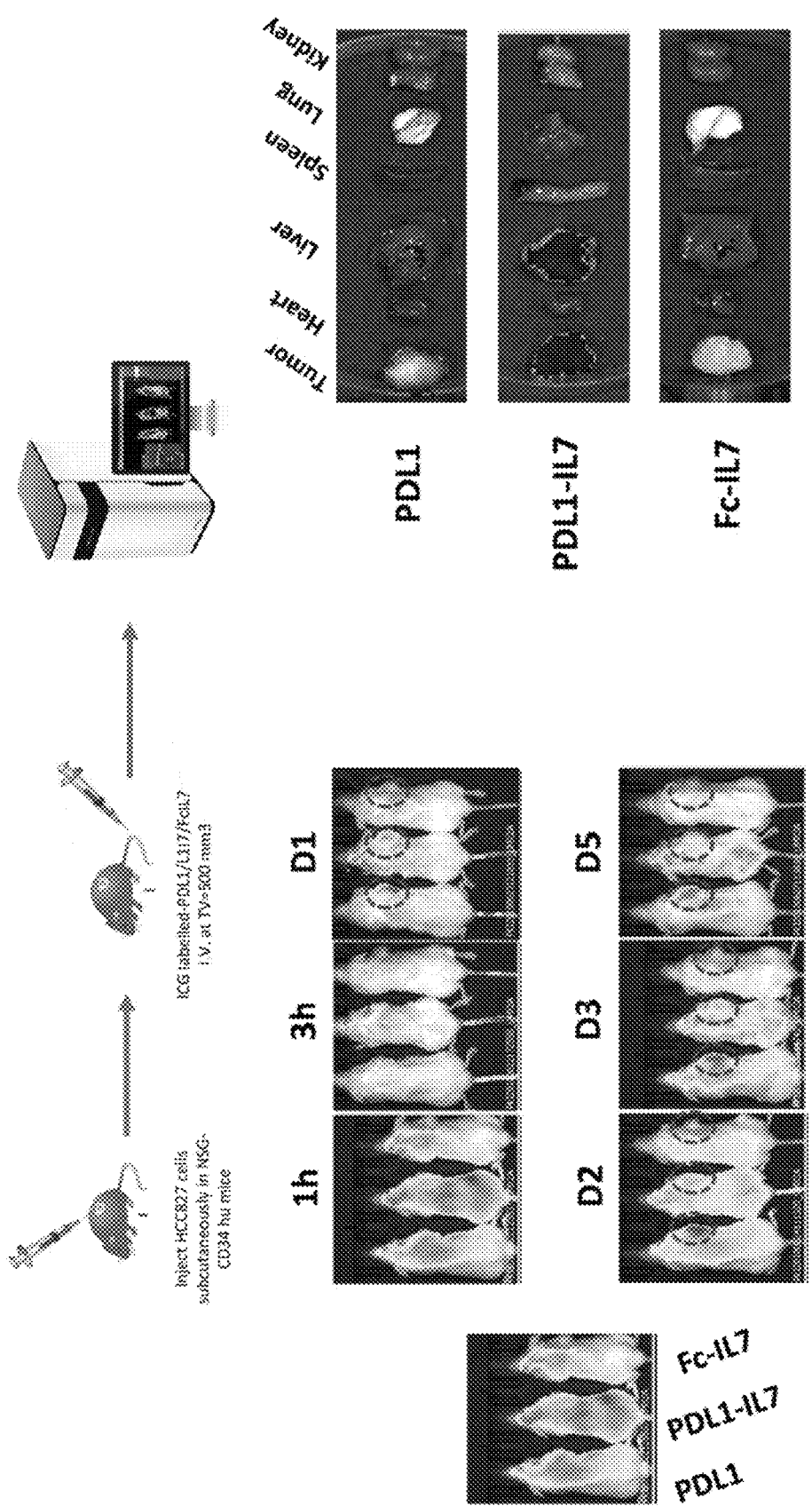
FIG. 9 shows that the tested fusion molecule, like anti-PDL1 antibody, was able to enrich in the tumor site.

To evaluate the distribution of anti-PDL1-IL7 fusion molecule in vivo, the in vivo tracking assay was conducted. Briefly, ICG-labeled anti-PDL1 mAb, anti-PDL1-IL7 or Fc-IL7 were injected into HCC827-transplanted CD34$^+$ hemopoietic stem cell (HSC) humanized mice intravenously when tumor size reached 500 mm$^3$. Imaging systems were used to capture the fluorescence signal at different time intervals. As shown in FIG. 9, similar to anti-PDL1 mAb, anti-PDL1-IL7 significantly enriched in the tumor site whereas the Fc-IL7 was widely spread especially at Day 1 after administration. These data collectively showed the selective and specific distribution of anti-PDL1-IL7, demonstrating the reduced systemic effect of IL7 in the fusion molecule.

Example 8: In Vivo Efficacy of Anti-PDL1-IL7 in PDL1-Therapy Resistant B16F10 Mice Model To evaluate the in vivo efficacy of anti-PDL1-IL7, PDL1 antibody resistant B16F10 melanoma syngeneic mice model was employed with surrogate anti-PDL1-IL7, a molecule comprised of two mouse IL7 fused with an anti-PDL1 antibody which were cross-reactive with mouse PDL1. At this time point, two isoforms of IgG with (hIgG1$^{N297A}$) or without (mIgG2a) ADCC function were used to evaluate the contribution of ADCC to the efficacy. Briefly, equal molar of anti-PDL1, mIL7-Fc, combination of these two molecules or fusion molecules were administrated s.c. to the C57/B16 mice at the day of B16F10 tumor cell transplantation and repeatedly every four days.

Figure 10:
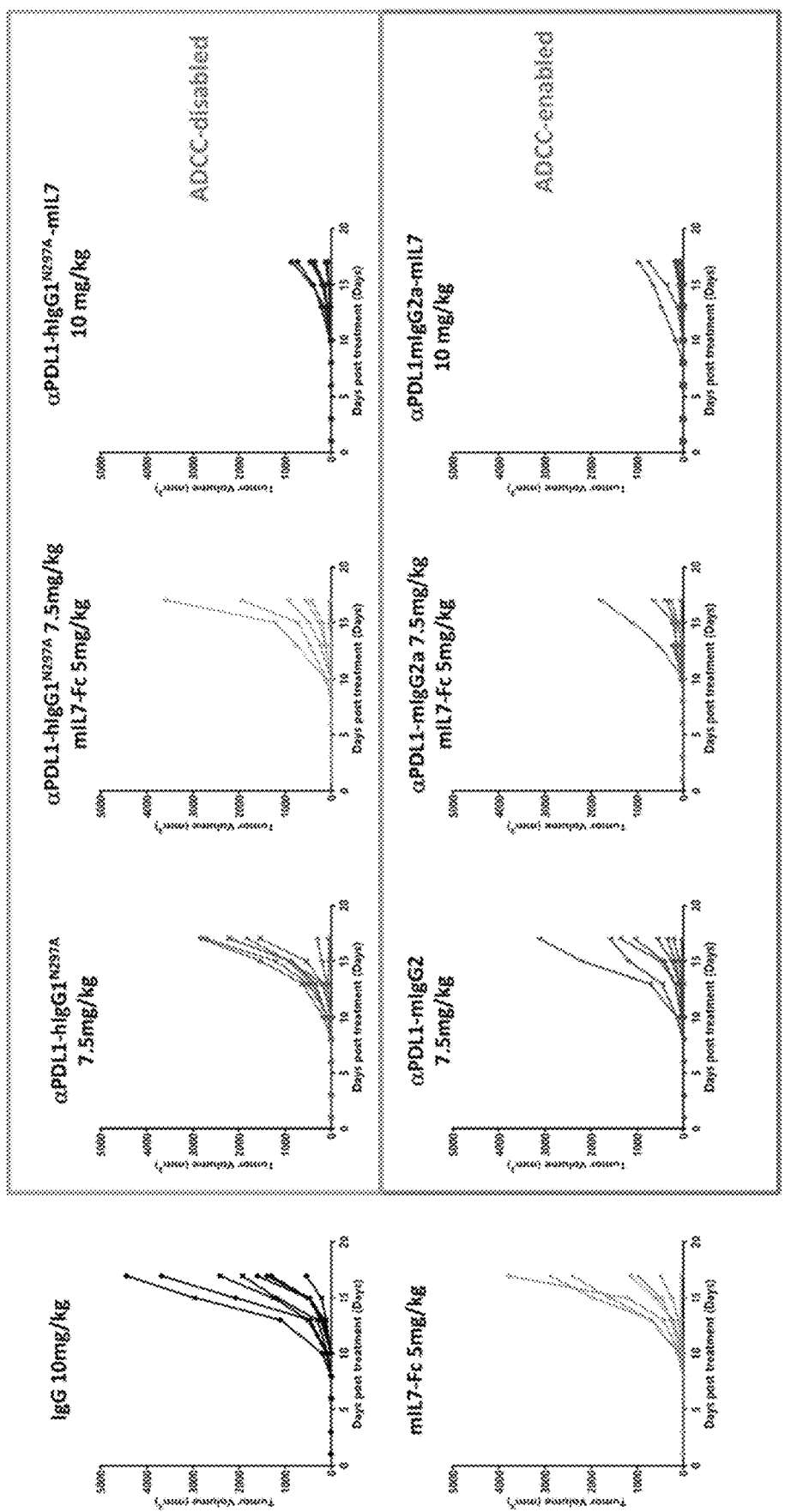
FIG. 10 shows the efficacy in tumor growth inhibition of various tested molecules.
Figure 11:
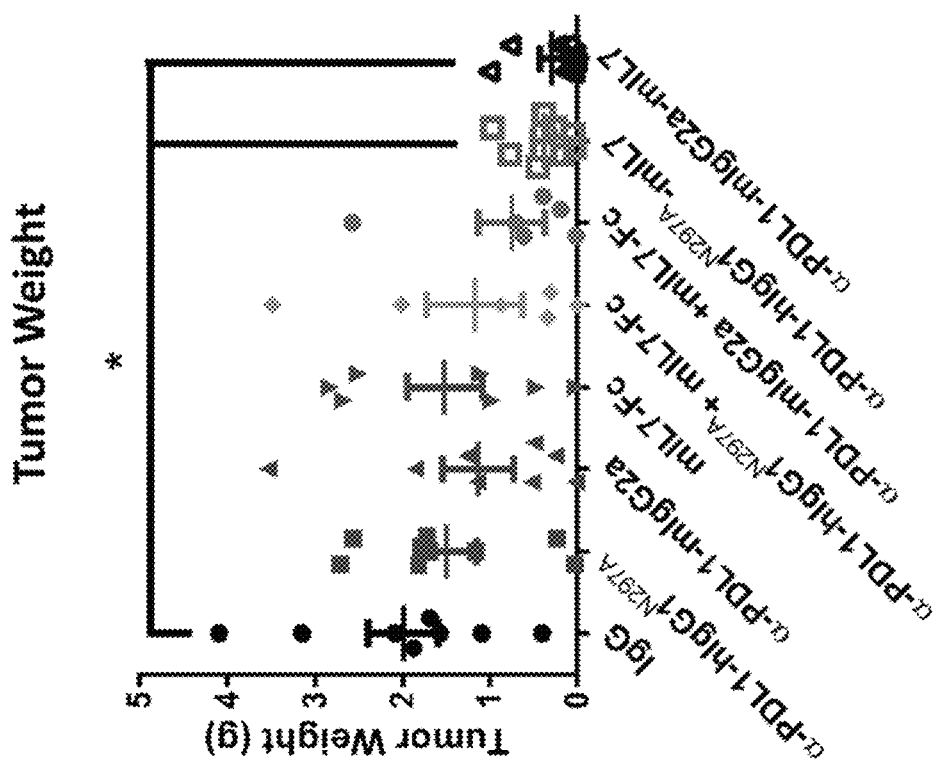
FIG. 11 presents the tumor weight of each animal at the end of the in vivo study.

As shown in FIG. 10, mIL7-Fc and ADCC-disabled anti-PDL1-hIgG1$^{N297A}$ monotherapy showed extremely weak efficacy in tumor growth inhibition (Tumor Growth Index (TGI)=22.5% and 21%, respectively). On the contrary, anti-PDL1-mIgG2a with enabled-ADCC function showed moderate attenuation of tumor growth (TGI=52.0%). Combination of anti-PDL1 mAb and mIL7 showed synergistic effect compared with their respective monotherapy both in ADCC-disabled and enabled groups, with more severe inhibition of tumor growth in ADCC-enabled groups (TGI=42.3% and 73.4%). More importantly, both fusion molecules (with and without ADCC function) show better efficacy in preventing tumor growth compared with combo-group (TGI=82.0% and 86.3%), indicating a mechanistical benefit of bifunctional molecule in site-specific control of tumor development. At the end of the experiment, tumor weights of each animals were measured. The tendency of the variation of tumor weights was similar to that of the tumor volume change (FIG. 11). These data indicated the contribution of ADCC to tumor growth control of anti-PDL1-IL7 molecules.

Figure 12:
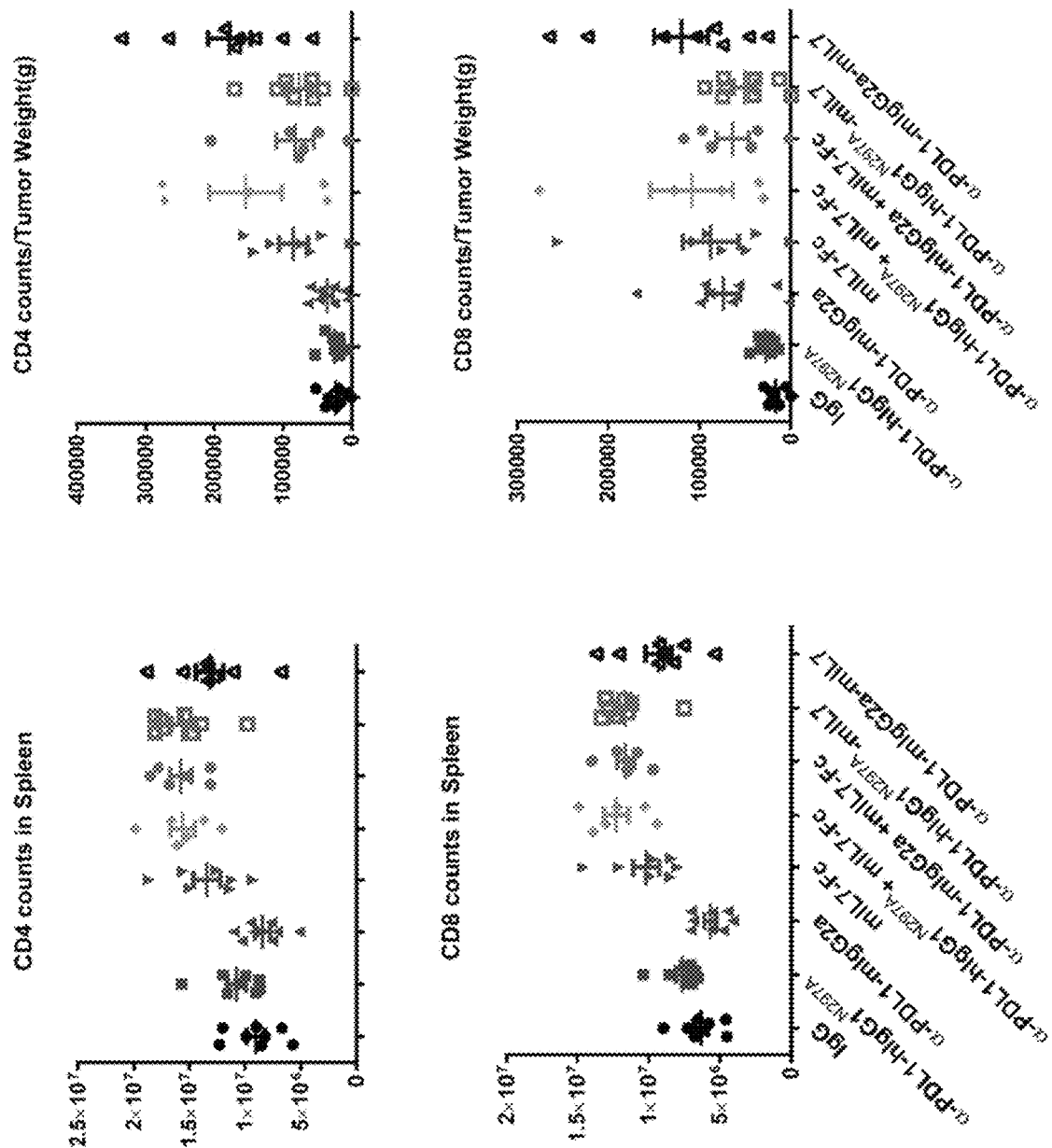
FIG. 12 presents data to show the absolute numbers of CD4$^+$ and CD8$^+$ T cells in spleen and tumor of each animal at the end of the in vivo study.

Next, absolute numbers of splenic and tumor infiltrating CD4$^+$ T and CD8$^+$ T cells were analyzed by FACS. Increase of splenic and tumor infiltrating CD4$^+$ T and CD8$^+$ T cells was observed in mIL-7-treatment-related groups, no matter mono-, combo-therapy or fusion molecule treatment, indicating IL7 played a role in enhancing T cell proliferation both in peripheral and in intra-tumor environment (FIG. 12). These data indicated that anti-PDL1-IL7 fusion molecule exhibited superior efficacy through combination of PDL1 antagonism effect with IL7-deriven T cell proliferation, resulting in a reinvigorated anti-tumor microenvironment.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A fusion molecule comprising an anti-PD-L1 antibody or antigen-binding fragment thereof fused, through a peptide linker, to a peptide comprising the amino acid sequence of SEQ ID NO:9.

2. The fusion molecule of claim 1, wherein the anti-PD-L1 antibody or the antigen-binding fragment thereof comprises a heavy chain variable region comprising CDR1, CDR2, and CDR3 having the amino acid sequences of residues 31-35, residues 50-66, and residues 99-108 of SEQ ID NO:6 respectively, and a light chain variable region comprising CDR1, CDR2, and CDR3 having the amino acid sequences of residues 24-34, residues 50-56, and residues 89-97 of SEQ ID NO:7 respectively.

3. The fusion molecule of claim 1, wherein the anti-PD-L1 antibody or the antigen-binding fragment thereof comprises a heavy chain variable region comprising the amino acid sequence of SEQ ID NO: 6, and a light chain variable region comprising the amino acid sequence of SEQ ID NO: 7.

4. The fusion molecule of claim 1, wherein the peptide linker is located N-terminal to the anti-PD-L1 antibody or antigen-binding fragment thereof.

5. An isolated cell comprising one or more polynucleotide encoding the fusion molecule of claim 1.

6. A method of treating a cancer in a patient in need thereof, comprising administering to the patient the fusion molecule of claim 1.

* * * * *

SEQUENCE LISTING

<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Gly Gly Gly Ser Gly Gly Gly Gly Ser
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 30
<212> TYPE: PRT
<213> ORGANISM: Artificial Sequence
<220> FEATURE:
<223> OTHER INFORMATION: Synthetic

<400> SEQUENCE: 3

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Gly Ser Gly Ser Gly Ser Gly Ser Gly Ser Gly Ser Gly Ser Gly Ser
1               5                   10                  15

Gly Ser

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Glu Pro Lys Ser Ser Asp Lys Thr His Thr Cys Pro Pro Cys Pro
1               5                   10                  15

<210> SEQ ID NO 6
<211> LENGTH: 119
<212> TYPE: PRT
<213> ORGANISM: Artificial Sequence
<220> FEATURE:
<223> OTHER INFORMATION: Synthetic

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 7
<211> LENGTH: 107
<212> TYPE: PRT
<213> ORGANISM: Artificial Sequence
<220> FEATURE:
<223> OTHER INFORMATION: Synthetic

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 8
<211> LENGTH: 152
<212> TYPE: PRT
<213> ORGANISM: Artificial Sequence
<220> FEATURE:
<223> OTHER INFORMATION: Synthetic

<400> SEQUENCE: 8

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

```
Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
            130                 135             140

Ile Leu Met Gly Thr Lys Glu His
145                 150

<210> SEQ ID NO 9
<211> LENGTH: 152
<212> TYPE: PRT
<213> ORGANISM: Artificial Sequence
<220> FEATURE:
<223> OTHER INFORMATION: Synthetic

<400> SEQUENCE: 9

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
            50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Ala Asn Lys
            130                 135             140

Ile Leu Met Gly Thr Lys Glu His
145                 150
```